United States Patent
Reizenson

(10) Patent No.: US 10,368,968 B2
(45) Date of Patent: Aug. 6, 2019

(54) ORAL HYGIENE SYSTEMS

(71) Applicant: Igor Reizenson, Alpharetta, GA (US)

(72) Inventor: Igor Reizenson, Alpharetta, GA (US)

(73) Assignee: Igor Reizenson, Alpharetta, GA (US)

( * ) Notice: Subject to any disclaimer, the term of this patent is extended or adjusted under 35 U.S.C. 154(b) by 0 days.

(21) Appl. No.: 15/845,467

(22) Filed: Dec. 18, 2017

(65) Prior Publication Data
US 2019/0183619 A1    Jun. 20, 2019

(51) Int. Cl.
| | | |
|---|---|---|
| A61C 17/22 | (2006.01) | |
| A61C 1/00 | (2006.01) | |
| A61C 17/20 | (2006.01) | |
| A61B 5/145 | (2006.01) | |
| A61B 5/00 | (2006.01) | |
| A61C 17/02 | (2006.01) | |
| A61B 10/00 | (2006.01) | |

(52) U.S. Cl.
CPC .......... *A61C 17/228* (2013.01); *A61B 5/0004* (2013.01); *A61B 5/14507* (2013.01); *A61B 10/0051* (2013.01); *A61C 1/0084* (2013.01); *A61C 17/0202* (2013.01); *A61C 17/20* (2013.01); *A61B 5/14532* (2013.01); *A61B 5/14546* (2013.01)

(58) Field of Classification Search
CPC ... A61C 1/0084; A61C 17/20; A61C 17/0211; A61C 17/222; A61C 17/32; A61C 17/046; A61C 17/228; A61C 17/0202; A46B 15/0012; A46B 9/045
See application file for complete search history.

(56) References Cited

U.S. PATENT DOCUMENTS

| | | | | |
|---|---|---|---|---|
| 5,542,845 A | * | 8/1996 | Jenkins | A61C 1/16 433/116 |
| 6,623,698 B2 | | 9/2003 | Kuo | |
| 6,893,259 B1 | * | 5/2005 | Reizenson | A61C 17/0211 433/29 |
| 2005/0196725 A1 | * | 9/2005 | Fu | A61C 17/0211 433/216 |

(Continued)

OTHER PUBLICATIONS

Chaplin, Steve, "Non-invasive blood glucose testing: the horizon," Practical Diabetes, vol. 33.9, Nov. 30, 2016 (9 pages).

(Continued)

*Primary Examiner* — Wade Miles
*Assistant Examiner* — Shannel N Wright
(74) *Attorney, Agent, or Firm* — Eversheds Sutherland (US) LLP

(57) ABSTRACT

Oral hygiene systems and methods for their use are provided. An oral hygiene system includes a mouthpiece having an outer portion and an inner portion configured to receive at least a portion of a user's dental and gum structures, a plurality of filaments disposed within the inner portion of the mouthpiece, a water pressure irrigator configured to be selectively coupled to the outer portion of the mouthpiece and to deliver fluid to the inner portion of the mouthpiece, and a fluid reservoir in fluid communication with the water pressure irrigator and configured to deliver the fluid thereto, wherein the system is configured to generate ultrasound/ultrasonic vibration within the inner portion of the mouthpiece.

16 Claims, 9 Drawing Sheets

(56) References Cited

U.S. PATENT DOCUMENTS

| | | | |
|---|---|---|---|
| 2009/0208898 A1* | 8/2009 | Kaplan | A46B 9/045 433/80 |
| 2009/0276972 A1* | 11/2009 | Dugan | A46B 7/00 15/167.2 |
| 2012/0219926 A1* | 8/2012 | Sullivan | A61C 17/0211 433/80 |
| 2015/0072300 A1* | 3/2015 | Wolpo | A61N 1/0428 433/27 |
| 2015/0328084 A1* | 11/2015 | Cash | A61J 7/0053 604/79 |
| 2016/0135581 A1* | 5/2016 | Pai | A46B 5/0095 433/216 |
| 2016/0338626 A1* | 11/2016 | Wang | A61C 19/04 |
| 2017/0007215 A1* | 1/2017 | Podoly | A61C 17/046 |
| 2017/0056143 A1* | 3/2017 | Hyun | A61C 17/02 |
| 2017/0056146 A1* | 3/2017 | Boughorbel | A46B 15/0004 |
| 2018/0153762 A1* | 6/2018 | Van Dijk | A61C 17/0202 |
| 2018/0311023 A1* | 11/2018 | Yao | A61C 17/28 |
| 2019/0000599 A1* | 1/2019 | Hanuschik | A61C 17/0211 |

OTHER PUBLICATIONS

Kim, Jayoung et al., "Non-invasive mouthguard biosensor for continuous salivary monitoring of metabolites," Analyst, Issue 7, 2014 (5 pages).

"Biological sensor can detect gluclose leveels in saliva more accurately and cost-efficiently than blood test," https://phys.org/news/2017-05-biological-sensor-gluclose-saliva-accurately.html (4 pages), May 2, 2017.

Blizzident high tech toothbrush review—YouTube, https://www.youtube.com/watch?v=15J1KqoU4cl&feature=youtu.be [retrieved on Dec. 19, 2017].

Do not lose time brushing your teeth: Amabrush does better, https://www.youtube.com/watch?v=K9YK-dg0-CU&feature=youtu.be [retrieved on Dec. 19, 2017].

* cited by examiner

ORAL HYGIENE SYSTEMS

TECHNICAL FIELD

The present disclosure relates generally to oral hygiene systems, and more particularly to ultrasonic oral hygiene systems.

BACKGROUND

In addition to regular professional dental checkups, daily oral hygiene is generally recognized as an effective preventative measure against the onset, development, and/or exacerbation of periodontal disease, gingivitis and/or tooth decay. The American Dental Association recommends brushing twice a day for at least two minutes, for a thorough clean. Furthermore, the Association recommends flossing or cleaning between your teeth at least once each day.

Many people do not follow the recommendations of the American Dental Association, and even those who do may not have the proper technique for brushing every surface of every tooth. Indeed, even the most meticulous individuals dedicated to thorough brushing and flossing practices often fail to reach, loosen and remove deep-gum and/or deep inter-dental bacterial plaque, tarter and/or food particulates. As such, most individuals must resort to biannual professional dental cleanings to remove such residual or vestigial bacteria, tarter deposits, and the like.

Accordingly, there is a need for improved in-home oral hygiene devices that encourage thorough brushing and flossing behaviors while increasing the effectiveness of brushing and flossing.

SUMMARY

In one aspect, an oral hygiene system is provided, including a mouthpiece having an outer portion and an inner portion configured to receive at least a portion of a user's dental and gum structures, a plurality of filaments disposed within the inner portion of the mouthpiece, a water pressure irrigator configured to be selectively coupled to the outer portion of the mouthpiece and to deliver fluid to the inner portion of the mouthpiece, a handle rigidly connected to the water pressure irrigator, and a fluid reservoir in fluid communication with the water pressure irrigator and configured to deliver the fluid thereto, wherein the system is configured to generate ultrasound/ultrasonic vibration within the inner portion of the mouthpiece.

In another aspect, an oral hygiene system is provided, including a mouthpiece having an outer portion and an inner portion configured to receive at least a portion of a user's dental and gum structures, a plurality of silicone filaments disposed within the inner portion of the mouthpiece, a water pressure irrigator configured to be selectively coupled to the outer portion of the mouthpiece and to deliver fluid to the inner portion of the mouthpiece, the water pressure irrigator comprising a wedge-shaped silicone tip having an elongated orifice, a handle rigidly connected to the water pressure irrigator, and a fluid reservoir in fluid communication with the water pressure irrigator and configured to deliver the fluid thereto, wherein the system is configured to generate ultrasound/ultrasonic vibration within the inner portion of the mouthpiece and at the tip of the water pressure irrigator.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

DETAILED DESCRIPTION

Oral hygiene systems suitable for in-home use and adapted to provide a user with effective dental and gingival cleansing, inter-dental and deep-gum bacterial plaque removal have been developed. These systems encourage users to meet recommend brushing and flossing standards by providing a relatively effortless and highly effective cleaning system, which may be utilized in conjunction with, or in lieu of, conventional brushing and/or flossing practices.

Figure 2:
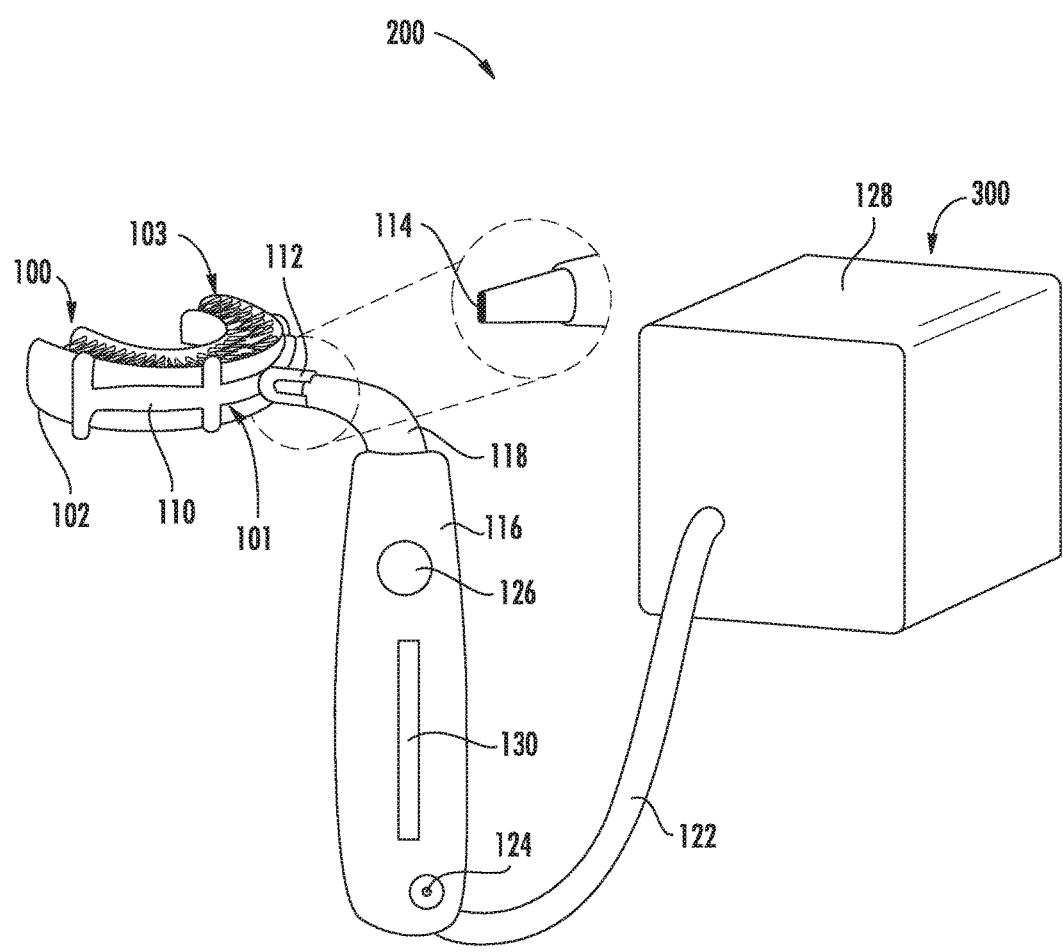
FIG. 2 is a perspective view of one embodiment of an oral hygiene system.

In certain embodiments, as shown in FIG. 2, an oral hygiene system 200 includes a mouthpiece 100 having an outer portion 101 and an inner portion 103 configured to receive at least a portion of a user's dental and gum structures, a plurality of filaments 106 disposed within the inner portion 103, a water pressure irrigator 118 (e.g., a water pick) configured to be selectively coupled to the outer portion 101 of the mouthpiece 100 and to deliver fluid to the inner portion 103 of the mouthpiece 100, a handle 116 rigidly connected to the water pressure irrigator 118, and a fluid reservoir 128 in fluid communication with the water pressure irrigator 118 and configured to deliver the fluid thereto. In some embodiments, the system 200 is configured to generate ultrasound/ultrasonic vibration within the inner portion 103 of the mouthpiece 100, so as to remove plaque from the user's teeth and gums and to render plaque bacteria within the mouth harmless. As used herein, the terms "ultrasound" and "ultrasonic vibration" are used interchangeably to refer to acoustic pressure waves having a frequency of 20 to 400 kilohertz—above the upper limit of human hearing. For example, the ultrasound/ultrasonic vibration generated within the mouthpiece and/or water pressure irrigator may have a frequency of about 1.6 MHz.

In some embodiments, the oral hygiene systems further include oscillating pulse (e.g., sonic vibration), cavitation (e.g., microbubbles), teeth bleaching/whitening, and/or biometric sample collection and analysis features, as will be described in greater detail below. As used herein, the term "oscillating pulse" is used to refer to vibration generated at or within the components of the systems described herein, such as the filaments, mouthpiece, and/or water pressure irrigator.

Various features of the systems and embodiments thereof are described below in greater detail.

Mouthpiece

The mouthpiece 100 may be of a size and shape suitable to be comfortably received by a human mouth. In some embodiments, as shown in FIGS. 1A-1D, the mouthpiece 100 may be configured to receive only the top or bottom teeth at a time. In other embodiments, as shown in FIG. 4, the mouthpiece 100 may be configured to receive both the top and bottom teeth at once.

In some embodiments, as shown in FIG. 1, the mouthpiece 100 includes two U-shaped walls 102 and a transverse wall 104 connecting the two U-shaped walls 102, to define the inner portion 103 of the mouthpiece 100, which is configured to receive either the top or bottom teeth. For example, the U-shaped walls may be parallel to one another and spaced from one another by a suitable width to accommodate the teeth and gums of a user, in addition to the filaments within the inner portion 103 of the mouthpiece 100. For example, the U-shaped walls 102 and the transverse walls 104 may be one piece of material or several pieces of material fused, molded, or otherwise connected by another process. In one embodiment, the mouthpiece 100 is made of a flexible material, such as silicone or another suitable material.

Figure 4:
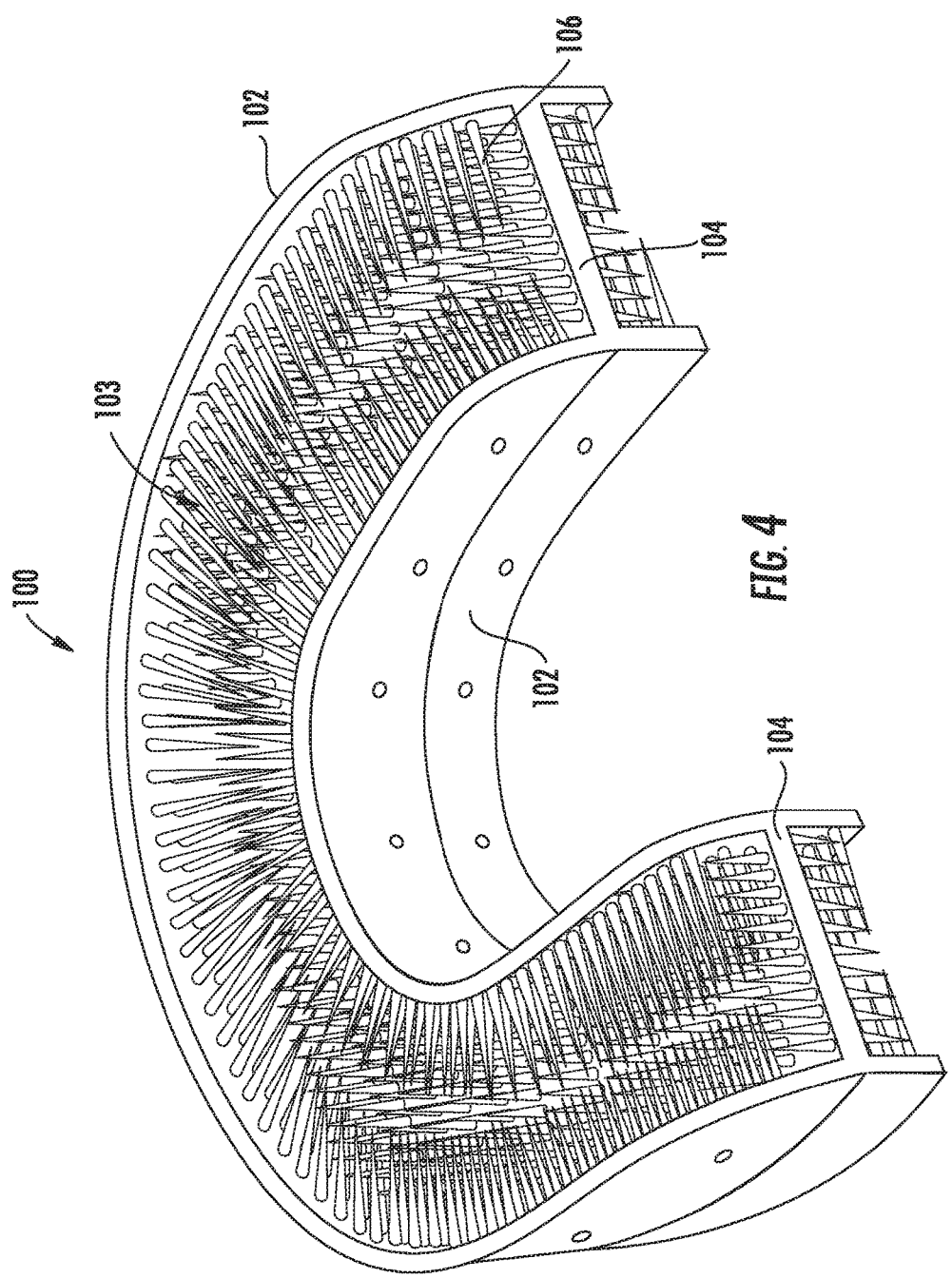
FIG. 4 is a perspective view of one embodiment of a mouthpiece of an oral hygiene system.
Figure 5A:
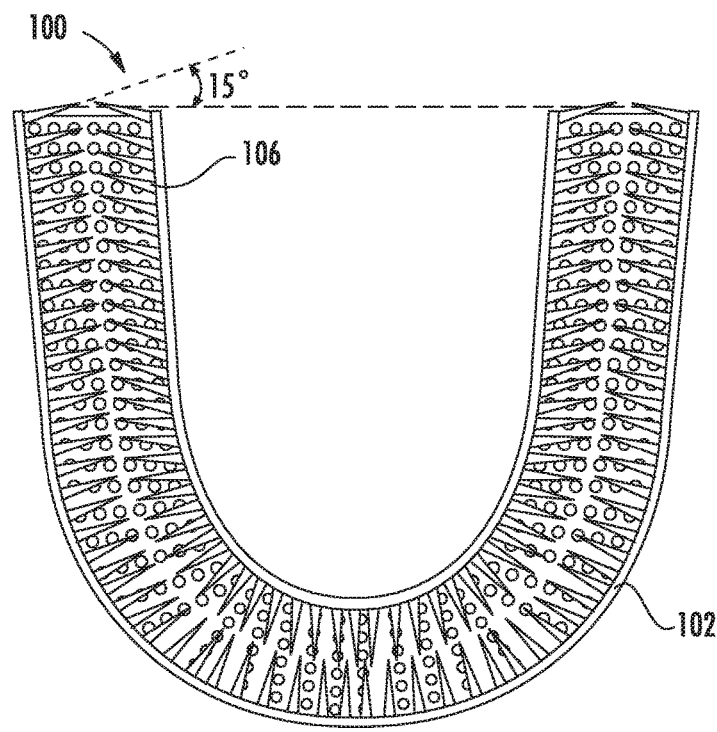
FIG. 5A is a top view of one embodiment of a mouthpiece of an oral hygiene device.
Figure 5B:
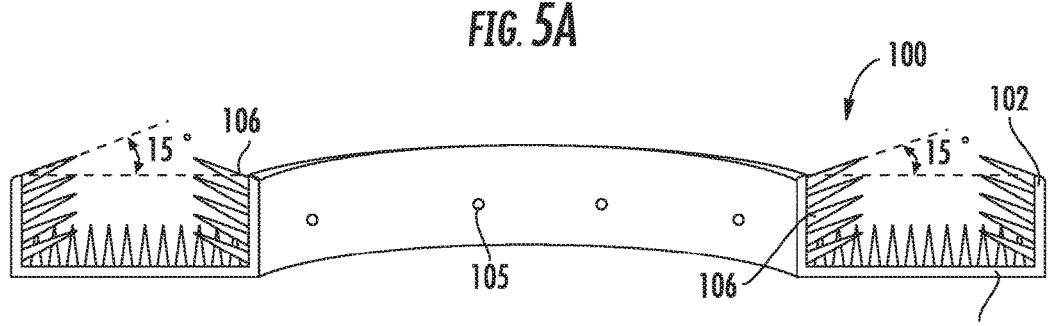
FIG. 5B is a cross-sectional front view of one embodiment of the mouthpiece of FIG. 5A.
Figure 6A:
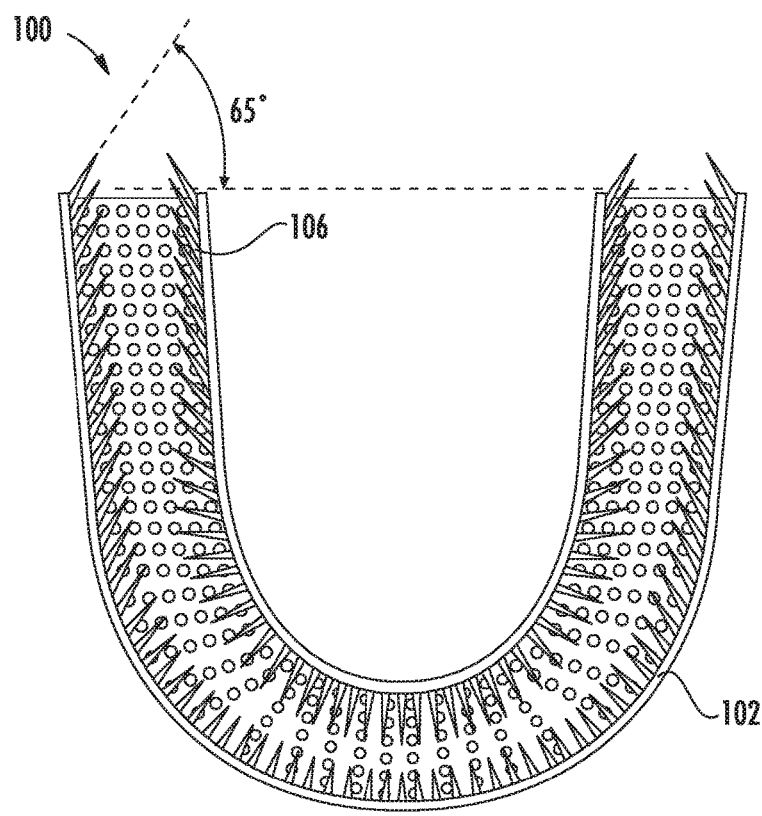
FIG. 6A is a top view of one embodiment of a mouthpiece of an oral hygiene device.
Figure 6B:
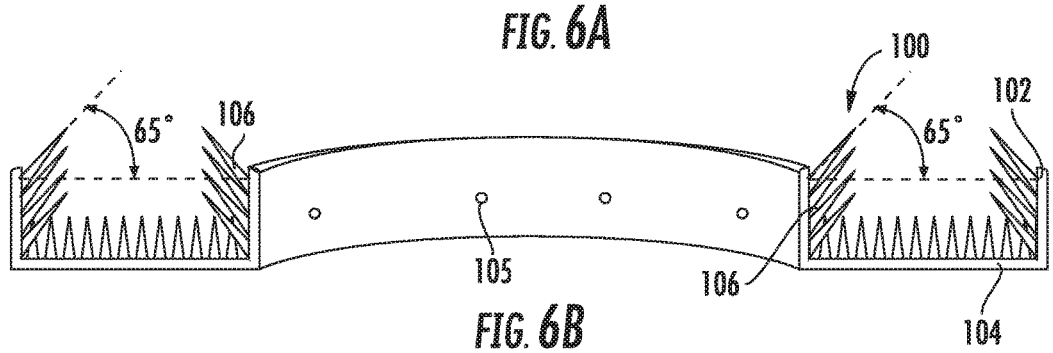
FIG. 6B is a cross-sectional front view of one embodiment of the mouthpiece of FIG. 6A.

In some embodiments, as shown in FIG. 4, the mouthpiece 100 includes two U-shaped walls 102 configured to receive both the top and bottom teeth at once. For example, the U-shaped walls 102 may be formed as a single piece or may be formed from multiple pieces that are coupled, directly or indirectly, to one another. In some embodiments, the mouthpiece 100 includes a transverse wall 104 connecting the two U-shaped walls, and bisecting the mouthpiece 100 into upper and lower sections for receiving the top and bottom teeth/gums, respectively.

As shown in FIGS. 1A-1D and 4, the mouthpiece 100 contains filaments 106. For example, the filaments 106 may protrude from one or both of the U-shaped walls 102 and/or from the transverse wall 104, such that the ends of the filaments are positioned to contact the teeth of a user wearing the mouthpiece. For example, the filaments 106 may be spaced evenly and may be numerous enough to create several rows and columns along the one or more walls. In certain embodiments, the filaments 106 are configured in the mouthpiece 100 such that both the front and rear surfaces of the teeth and gums are contacted by the filaments 106, and are therefore cleaned during operation of the system.

Figure 1A:
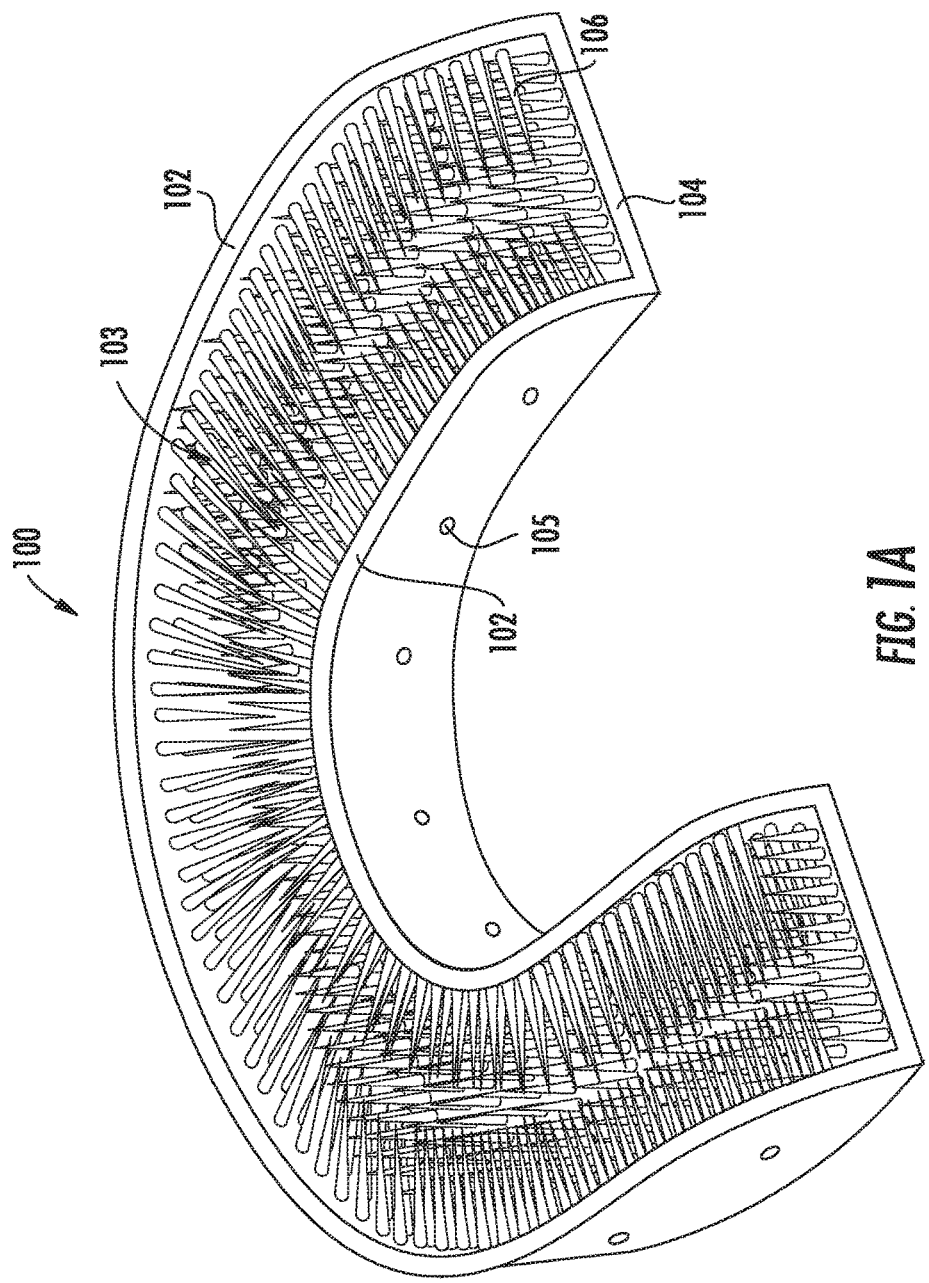
FIG. 1A is a top perspective view of one embodiment of a mouthpiece of an oral hygiene system.
Figure 1B:
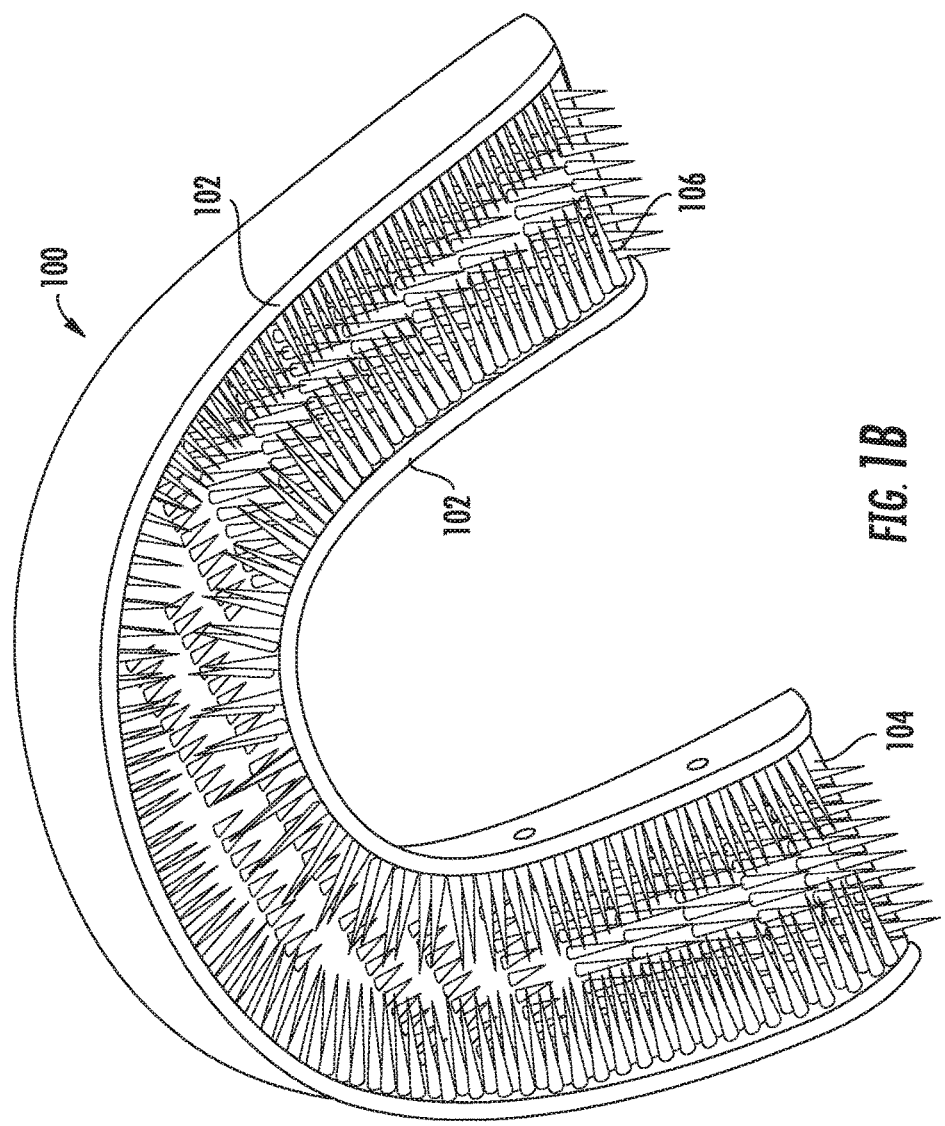
FIG. 1B is a top perspective view of one embodiment of the mouthpiece of FIG. 1A.
Figure 1C:
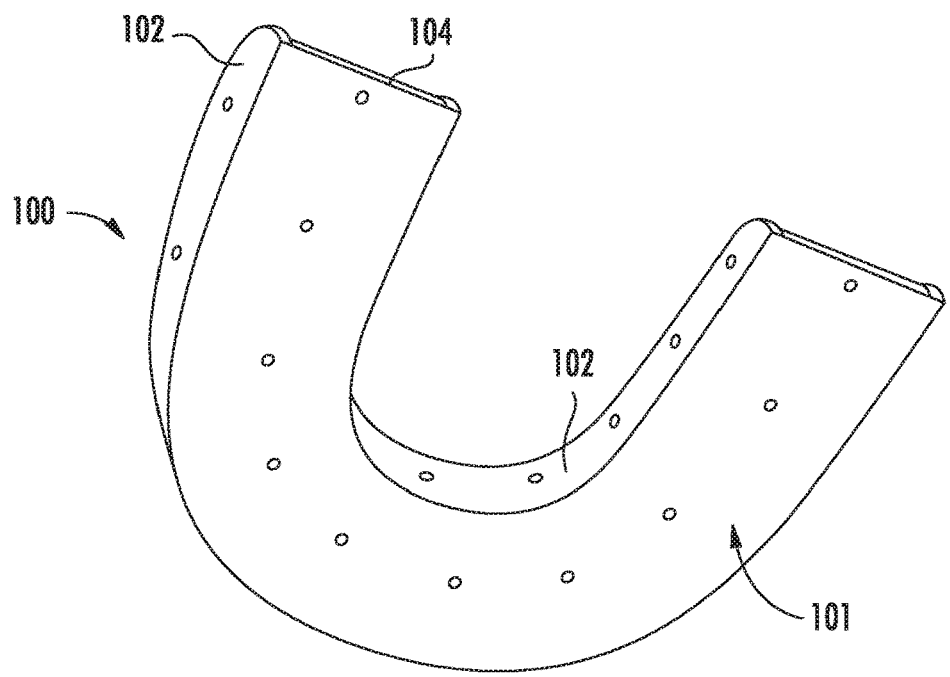
FIG. 1C is a bottom perspective view of one embodiment of the mouthpiece of FIG. 1A.
Figure 1D:
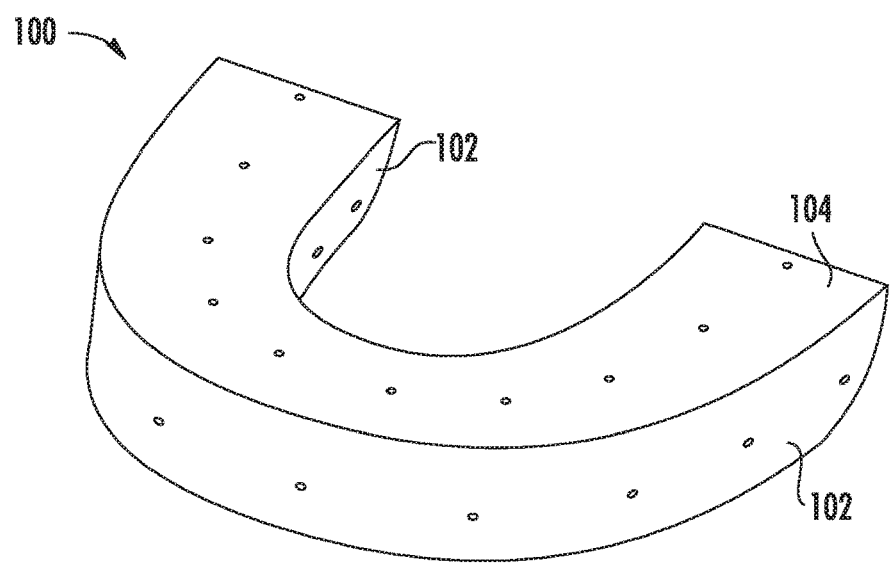
FIG. 1D is a bottom perspective view of one embodiment of the mouthpiece of FIG. 1A.

In certain embodiments, as shown in FIG. 1A, the filaments 106 project perpendicularly from each of the U-shaped walls and traverse wall from which they extend. However, the filaments 106 may project at any suitable angle, such as from about 10 degrees to about 90 degrees, relative to the surface of the wall from which they extend, to provide suitable contact with the teeth of a user wearing the mouthpiece. In certain embodiments, filaments of varying angles extend from the surfaces of the mouthpiece walls.

Figure 7:
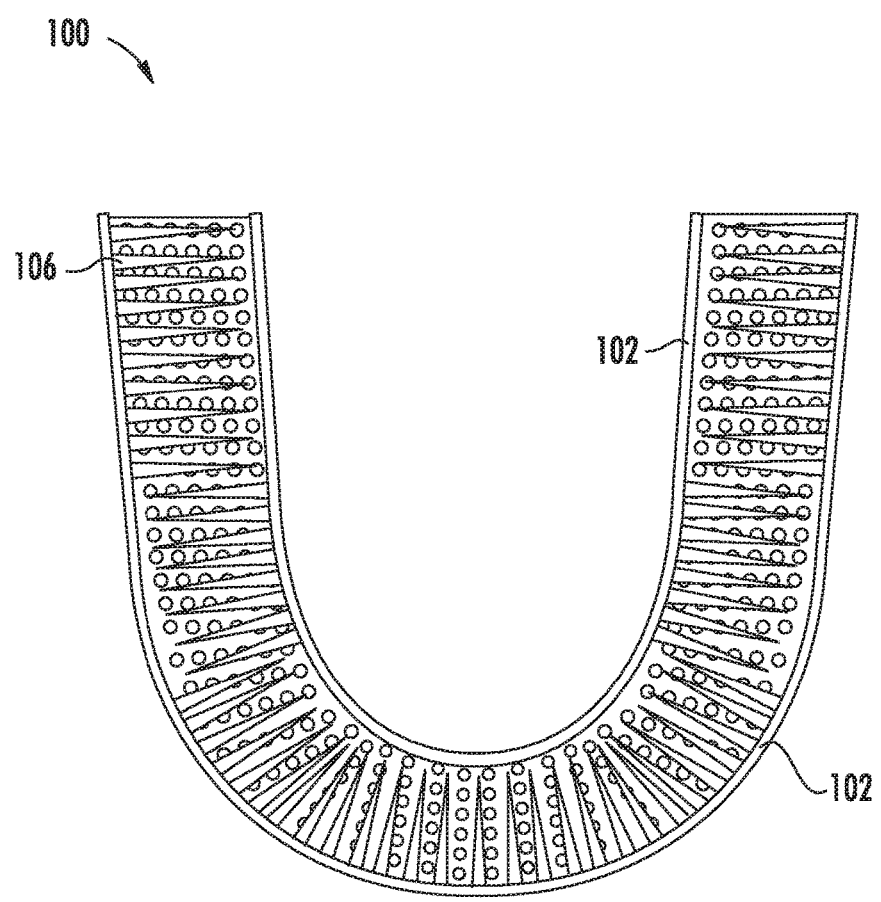
FIG. 7 is a top view of one embodiment of a mouthpiece of an oral hygiene device.

For example, the filaments 106 may be cylindrical, conical, frustoconical, or another suitable shape. The filaments 106 may be formed from a flexible material configured to flex to contact the teeth and to vibrate, such as in response to sonic vibration of the mouthpiece/handle. For example, the filaments 106 may be formed from silicone. For example, the filaments may have a Shore durometer in the range of less than about 50 A, such as from about 10OO to about 80OO, or from about 10OO to about 30 A. In some embodiments, as shown in FIGS. 1A-6B, the filaments 106 are placed at an equal distance from each other. In other embodiments, as seen in FIG. 7, the filaments 106 are grouped in a various configuration or pattern. For example, the filaments 106 may be disposed in a circular, rectangular, triangular, or other type of grouped pattern. The filaments 106 may extend from about a quarter of the distance to the opposite wall 102, about half the distance to the opposite wall 102, or even about the entire width of the mouthpiece to the opposite wall 102. For example, the filaments 106 for some distance of the mouthpiece 100 may exist only on one side of the mouthpiece. As seen in FIG. 7, the filaments 106 may form a pattern where the filaments are absent along a length of the wall in favor of filaments 106 extending from the opposite wall 102. Such patterns or configurations may be selected to maximize the effectiveness of the cleaning action provided by the filaments, such as positioning those filaments at particular positions of a user's teeth and/or gums.

In certain embodiments, as shown in FIGS. 5A-6B, the filaments are angled relative to a perpendicular plane intersecting the wall 102 from which they extend. For example, the filaments may be angled from said perpendicular plane at about a 15-degree angle towards a user's gums or angled at about a 65-degree angle toward a user's gums. The filaments may also angle away from a user's gums (i.e., toward the interior of the mouthpiece). The angle of the filaments may range from about 0 degrees (i.e., perpendicular to the plane of the wall 102 at the point at which the filament connects thereto), as shown in FIG. 1A, to about 90 degrees. The filaments along a similar wall of a mouthpiece may point in a similar angle. Alternatively, the filaments along a similar wall of a mouthpiece may point in opposing directions/angles. Thus, the filaments of the present systems may be distinct from traditional toothbrush bristles.

In certain embodiments, as shown in FIG. 1A, the mouthpiece 100 contains one or more apertures 105 extending from the outer portion to the inner portion of the mouthpiece 100. For example, these apertures may provide a pathway for fluid (e.g., saliva, water) within the mouth to enter the inner portion of the mouthpiece to act as a wetting agent, or vice versa, for fluid within the inner portion of the mouthpiece to flow out of the inner portion.

In certain embodiments, as shown in FIG. 2, the mouthpiece also includes a channel 110 extending along the outer portion 101 of the mouthpiece, such that fluid delivered from the water pressure irrigator 118 travels along the channel 110 and into the inner portion 103 of the mouthpiece 100. For example, a fluid connector 112 may be associated (e.g., in fluid connection) with the channel 110 and configured to securely couple the water pressure irrigator 118 to the mouthpiece 100. In some embodiments, the channel 110 is configured to deliver the fluid from the water pressure irrigator 118 to one or more positions at or adjacent the edge of wall 102, such that the fluid flows into the inner portion 103 from the edge of the wall 102. In some embodiments, the channel 110 is in fluid communication with one or more apertures 105, such that fluid is delivered to the inner portion 103 through the apertures. In some embodiments, the channel 110 may deliver fluid to the inner portion 103 through both of these means. For example, the channel 110 and fluid connector 112 may be securely or removably coupled (e.g., directly or indirectly) to wall 102.

In certain embodiments, the fluid connector 112 is configured to securely, but removably, receive the tip area 114 of the water pressure irrigator 118, such that a user may easily transform the system between the mouthpiece and water pressure irrigator configurations. For example, the fluid connector 112 may include a receiving cavity that is sized and shaped to securely but removably receive the tip area 114 of the water pressure irrigator. For example, the fluid connector 112 may couple to the water pressure irrigator 118 by any suitable means, including, but not limited to, friction fit, snap fit, threaded fit, or other suitable connections mechanisms.

In certain embodiments, the system is further configured to generate an oscillating pulse and/or microbubbles (e.g., through cavitation) within the inner portion of the mouthpiece. For example, the oscillating pulse may be effective to vibrate the filaments within the inner portion, to provide a scrubbing or brushing action. In one embodiment, the oscillating pulse is a sonic vibration.

Water Pressure Irrigator and Handle

Figure 3:
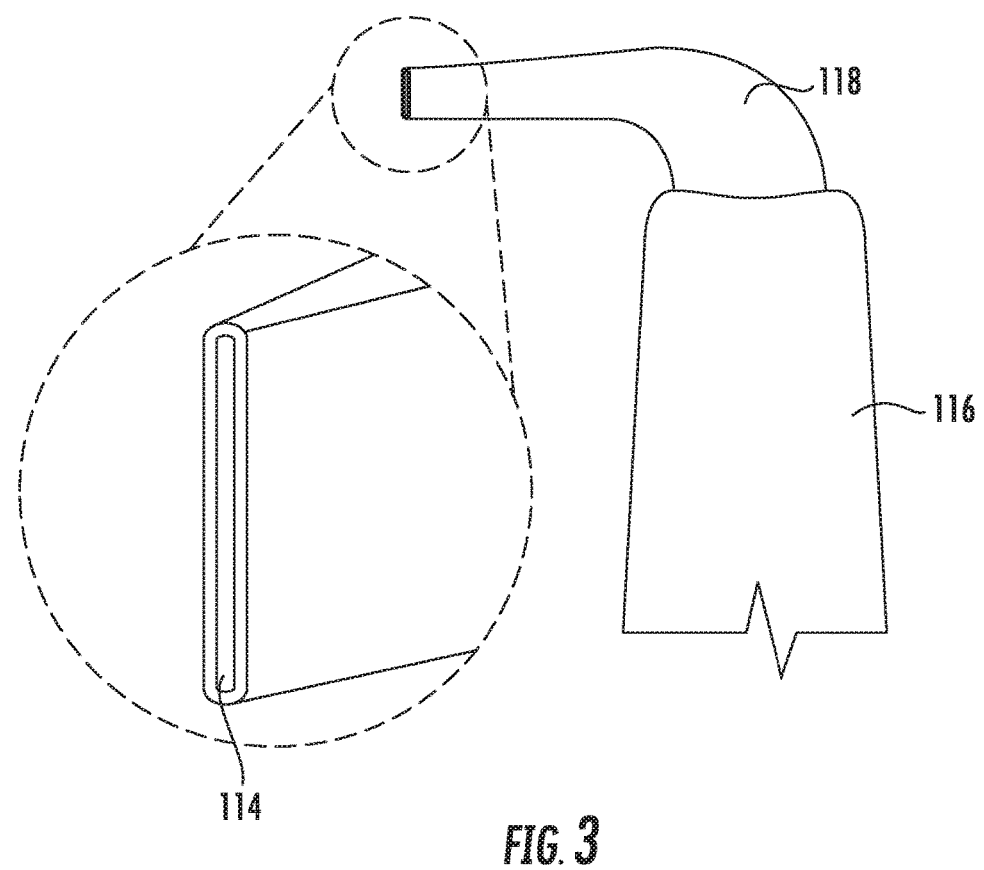
FIG. 3 is a perspective view of one embodiment of a water pressure irrigator of an oral hygiene system.

As shown in FIGS. 2 and 3, in certain embodiments, the water pressure irrigator 118 includes a tip area 114 that is sized and shaped for contacting the teeth and gums, the tip area containing an orifice for delivering fluid from the water pressure irrigator 118. For example, as shown in FIGS. 2 and 3, the water pressure irrigator 118 may have a wedge-shaped tip area 114 with an elongated orifice (e.g., an oval, elliptical, or rectangular shaped orifice). Thus, in some embodiments, the water pressure irrigator is not conical or frusto-conical in shape. It has been found that the wedge-shaped water pressure irrigator tip area 114 with elongated orifice provides improved teeth cleaning and flossing-type action. For example, the elongated orifice and wedge-shaped tip may be capable of cleaning a greater surface area and cleaning between teeth in the embrasures (e.g., as a substitute for flossing by contacting the areas between the teeth).

In certain embodiments, in addition to the pressurized fluid delivered from the water pressure irrigator 118, the system 200 is configured to generate ultrasound/ultrasonic vibration at the tip area 114 of the water pressure irrigator 118, so as to enhance the plaque removal and cavitation at the tip area. In one embodiment, an oscillating pulse may also be generated at the tip area 114 of the water pressure irrigator 118.

In certain embodiments, at least the tip area of the water pressure irrigator 118 is formed of a semi-flexible silicone or other suitable material.

As discussed above, the orifice of the tip area 114 of water pressure irrigator 118 is configured to selective coupling to the fluid connector 112 of the mouthpiece 100.

In certain embodiments, the water pressure irrigator 118 is rigidly coupled (directly or indirectly) to handle 116. For example, the handle 116 may provide a graspable surface for a user to hold and maneuver the water pressure irrigator 114 and mouthpiece 100, in use. For example, the handle may be any suitable size, shape, and design.

In certain embodiments, the ultrasonic and/or oscillating pulse generating elements are provided within the handle. For example, the handle may contain a suitable ultrasound/ultrasonic vibration generating transducer, such as one containing a piezoelectric crystal. For example, the handle may contain a suitable motor for generating an oscillating pulse (e.g., sonic vibration). That is, the handle 116 may deliver the ultrasound/ultrasonic vibration and/or oscillating pulse to the water pressure irrigator 118 and/or to the inner portion 103 of the mouthpiece 100.

In one embodiment, as shown in FIG. 2, the handle 116 has an actuating button 126 to allow a user to power the device on or off. In some embodiments, as shown in FIG. 2, the handle 116 has a tubular fluid connection 122 extending from the end opposite the water pressure irrigator 118 to a fluid reservoir 128.

In one embodiment, the handle 116 includes a level indicator 130. For example, the level indicator 130 may display the strength of the oscillating pulse or of the ultrasonic vibration. For example, the level indicator 130 may display the speed of water traveling through the tubular connection 122.

In some embodiments, the mouthpiece 100, or a separate mouthpiece that may be combined with mouthpiece 100 and system 200 in the form of a kit, may contain an optical fiber configured to deliver light within the mouthpiece, such as for teeth bleaching. In some embodiments, the handle 116 may include a light source, such as may be powered on or off by button 124. For example, the light source may be a LED or a small bulb, among others. For example, the light source 124 may be an ultraviolet light to whiten teeth or a blue light that accelerates bleaching.

Fluid Reservoir

In certain embodiments, the tubular fluid connection 122 is connected to a fluid reservoir 128. For example, the reservoir 128 may contain water, cleaning fluid, toothpaste, mouthwash, or some combination thereof. For example, the reservoir 128 may contain a pump that is effective to pump the fluid(s) through the tubular connection 122 and into the water pressure irrigator 118. For example, the pump may be suitable to provide a pressurized fluid stream suitable for loosening and/or removing plaque from the orifice of the water pressure irrigator 118.

In certain embodiments, the reservoir 128 is housed within a unit 300 that contains further electrical, electronic, or other components of the system 200. For example, unit 300 may contain a UV light area configured to receive the mouthpiece 100 of the system for cleaning.

In certain embodiments, the system 200 also includes a saliva analysis unit configured to analyze a sample of saliva collected by the water pressure irrigator 118 or mouthpiece 100 for blood sugar level, the presence of enzymes or protein markers, or both. For example, the system 200 may be configured to analyze blood sugar levels in the saliva as an alternative to blood testing for diabetics. For example, the system 200 may be configured to test saliva for a variety of protein markers that flag for cancer as well as other illnesses that cause inflammatory cell production. In one embodiment, the mouthpiece 100 is configured to collect a saliva sample for analysis. In one embodiment, the tip of the water pressure irrigator 118 is configured to collect a saliva sample for analysis. For example, the analysis may happen at the site of collection (e.g., at the mouthpiece or water pressure irrigator) or may happen within a portion of unit 300 configured to receive the sample from the collection site.

In certain embodiments, the system 200 is further configured to collect, store, and/or transmit the analyzed data to the patient's APP to chart data, as well as transmit to a doctor/caregiver for their review and storage. Thus, the system 200 may be configured to monitor the health of one or more users. In some embodiments, a transmitter within the unit 300 sends information wirelessly or by a wired connection. The unit 300 may also be configured to display certain collected information, such as a patient's detected glucose level.

Thus, in some embodiments, the present disclosure provides a dental bio sensor system for cleaning teeth and monitoring blood glucose levels within saliva. For example, the system may be useful for combining multiple daily hygienic routines for those with diabetes. For example, the system may clean teeth more effectively than manual brushing. For example, the system may also be less painful and more accommodating to diabetic individuals who use a prick to draw blood for blood glucose testing.

In one embodiment, an oral hygiene system includes a mouthpiece having an outer portion and an inner portion configured to receive at least a portion of a user's dental and gum structures, a plurality of silicone filaments disposed within the inner portion of the mouthpiece, a water pressure irrigator configured to be selectively coupled to the outer portion of the mouthpiece and to deliver fluid to the inner portion of the mouthpiece, the water pressure irrigator comprising a wedge-shaped silicone tip having an elongated orifice, a handle rigidly connected to the water pressure irrigator, and a fluid reservoir in fluid communication with the water pressure irrigator and configured to deliver the fluid thereto, wherein the system is configured to generate ultrasound/ultrasonic vibration within the inner portion of the mouthpiece and at the tip of the water pressure irrigator.

In use, a user inserts the mouthpiece 100 into his or her mouth, situating the teeth and gums within the inner portion 103 such that the filaments 106 are adjacent or contacting the teeth/gums. A suitable toothpaste (e.g., a foaming ISO toothpaste, or other known toothpaste) may be applied within the inner portion 103 prior to insertion. The user then activates the ultrasound/ultrasonic vibration and/or oscillating pulse features of the system, such that microbubbles/cavitation, filament scrubbing action, and/or plaque loosening and removal. In addition, fluid may flow from the mouth and/or water pressure irrigator (e.g., through the channel) into the inner portion 103 to provide any necessary wetting of the teeth and gums. Beneficially, the mouthpiece will effectively clean the chewing surfaces of the teeth and gums. This may replace the traditional toothbrush because it will give a much more thorough cleaning than a traditional toothbrush. For example, the system 200 may be configured to operate for a predetermined period upon a user powering up the device, such as 2 minutes, 1 minute, or 30 seconds.

Once the period has expired or the user is done with the scrubbing of chewing surfaces of teeth and gums, the user removes the mouthpiece from the handle, and the handle now becomes a water pressure irrigator that the user can operate to blast out plaque and food particles from between the teeth (i.e., instead of floss) and to contact/touch the water pressure irrigator tip in between the teeth to ultrasonically loosen all plaque and food particles as they are blasted out by water pressure. The used, "dirty" fluid in the mouth is able to be dribbled out of the mouth into the sink, in a way similar to traditional tooth brushing or water pressure irrigator operations.

While the disclosure has been described with reference to a number of embodiments, it will be understood by those skilled in the art that the invention is not limited to such disclosed embodiments. Rather, the invention can be modified to incorporate any number of variations, alterations, substitutions, or equivalent arrangements not described herein, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. An oral hygiene system, comprising:
a mouthpiece having an outer portion and an inner portion configured to receive at least a portion of a user's dental and gum structures;
a plurality of filaments disposed within the inner portion of the mouthpiece;
a water pressure irrigator configured to be selectively coupled, in a first configuration, to the outer portion of the mouthpiece and to deliver fluid to the inner portion of the mouthpiece when in the first configuration, and to be selectively decoupled from the mouthpiece in a second configuration, in which a tip area of the water pressure irrigator is sized and shaped to deliver fluid to the user's dental and gum structures, independent of the mouthpiece;
a handle rigidly connected to the water pressure irrigator; and
a fluid reservoir in fluid communication with the water pressure irrigator and configured to deliver the fluid thereto,
wherein the system is configured to generate ultrasound within the inner portion of the mouthpiece.

2. The oral hygiene system of claim 1, wherein:
the tip area of the water pressure irrigator comprises a wedge-shaped tip having an elongated orifice, and
the system is further configured to generate ultrasound at the tip of the water pressure irrigator.

3. The oral hygiene system of claim 1, wherein the mouthpiece further comprises a channel extending along the outer portion of the mouthpiece, such that fluid delivered from the water pressure irrigator travels along the channel and into the inner portion of the mouthpiece.

4. The oral hygiene system of claim 1, wherein each of the plurality of filaments is formed of silicone.

5. The oral hygiene system of claim 1, wherein the mouthpiece comprises a pair of opposed U-shaped walls and a transverse connecting wall, which together define the inner portion.

6. The oral hygiene system of claim 5, wherein the plurality of filaments project from each of the U-shaped walls and the connecting wall, at angles of from about 10 to about 90 degrees, relative to a surface of each wall.

7. The oral hygiene system of claim 5, wherein the plurality of filaments project perpendicularly from each of the U-shaped walls and the connecting wall.

8. The oral hygiene system of claim 1, wherein the system is further configured to generate an oscillating pulse within the inner portion of the mouthpiece.

9. The oral hygiene system of claim 8, wherein the oscillating pulse is a sonic vibration.

10. An oral hygiene system, comprising:
a mouthpiece having an outer portion and an inner portion configured to receive at least a portion of a user's dental and gum structures;
a plurality of silicone filaments disposed within the inner portion of the mouthpiece;
a water pressure irrigator configured to be selectively coupled to the outer portion of the mouthpiece and to deliver fluid to the inner portion of the mouthpiece, the water pressure irrigator comprising a wedge-shaped silicone tip having an elongated orifice;

a handle rigidly connected to the water pressure irrigator; and a fluid reservoir in fluid communication with the water pressure irrigator and configured to deliver the fluid thereto, wherein the system is configured to generate ultrasound within the inner portion of the mouthpiece and at the tip of the water pressure irrigator.

11. The oral hygiene system of claim 10, wherein the mouthpiece further comprises a channel extending along the outer portion of the mouthpiece, such that fluid delivered from the water pressure irrigator travels along the channel and into the inner portion of the mouthpiece.

12. The oral hygiene system of claim 10, wherein the mouthpiece comprises a pair of opposed U-shaped walls and a transverse connecting wall, which together define the inner portion.

13. The oral hygiene system of claim 12, wherein the plurality of filaments project from each of the U-shaped walls and the connecting wall, at angles of from about 10 to about 90 degrees, relative to a surface of each wall.

14. The oral hygiene system of claim 12, wherein the plurality of filaments project perpendicularly from each of the U-shaped walls and the connecting wall.

15. The oral hygiene system of claim 10, wherein the system is further configured to generate an oscillating pulse within the inner portion of the mouthpiece.

16. The oral hygiene system of claim 15, wherein the oscillating pulse is a sonic vibration.

\* \* \* \* \*